United States Patent [19]

Miyazawa et al.

[11] Patent Number: 4,770,821

[45] Date of Patent: Sep. 13, 1988

[54] METHOD FOR PREPARING β-CHLOROPIVALOYL CHLORIDE

[75] Inventors: Kenichi Miyazawa, Shimizu; Osamu Furusawa, Fuji, both of Japan

[73] Assignee: Ihara Nikkei Chemical Industry Co., Ltd., Shizuoka, Japan

[21] Appl. No.: 870,028

[22] Filed: Jun. 3, 1986

[30] Foreign Application Priority Data

Jun. 5, 1985 [JP] Japan ................................ 60-121843

[51] Int. Cl.$^4$ ............................................ C07C 58/03
[52] U.S. Cl. ................................................. 260/544 Y
[58] Field of Search ..................................... 260/544 Y

[56] References Cited

PUBLICATIONS

Groggins, P. H. *Unit Processes in Organic Synthesis,* 5th Ed. (1958) McGraw-Hill, publ., pp. 212 222-226.

*Primary Examiner*—Paul J. Killos
*Attorney, Agent, or Firm*—Birch, Stewart, Kolasch & Birch

[57] ABSTRACT

There is provided a method for preparing β-chloropivaloyl chloride which includes chlorinating pivalic acid to form pivaloyl chloride and reacting the resultant pivaloyl chloride with a chlorine gas in a gaseous phase to form β-chloropivaloyl chloride. Both steps may be carried out by a continuous process or a batch process. According to this method, the chlorination in the second step can be achieved at a low temperature, and the formation of by-products is reduced and production efficiency can be enhanced.

12 Claims, 2 Drawing Sheets

METHOD FOR PREPARING β-CHLOROPIVALOYL CHLORIDE

BACKGROUND OF THE INVENTION

1. Field of the Invention

The present invention relates to a method for preparing β-chloropivaloyl chloride by the chlorination of pivalic acid.

2. Description of the Prior Art

β-Chloropivaloyl chloride (α,α-dimethyl-β-chloropropionyl chloride) is important as an intermediate for the synthesis of various compounds. Specifically, it is useful for the synthesis of, for example, pesticides. Japanese Patent Publication No. 46046/1972 describes a method of preparing β-chloropivalic acid. According to this method, a chlorine gas is introduced into a distillation tower to contact with liquid phase pivalic acid, while the latter is refluxed in the distillation tower, and the resultant β-chloropivalic acid is collected on the bottom of the tower by means of a distillation effect, followed by removing the product. Then, β-chloropivalic acid may be allowed to react with phosgene, thionyl chloride or the like, thereby forming β-chloropivaloyl chloride.

The above mentioned method for preparing β-chloropivalic acid in Japanese Patent Publication No. 46046/1972 produces a smaller amount of dichloro-compounds and is considered to be superior, as compared with another method of directly blowing chlorine into pivalic acid. From the viewpoint of an industrial practice, however, this method has problems such as a temperature rise of up to 222° C. on a tower bottom, the installation of a reaction apparatus using a specific heat transfer medium, the formation of decomposition products and polymers due to the heat history of the reaction solution, and the like.

When it is attempted to carry out the operation under a reduced pressure for the purpose of solving these problems, there will occur other problems of the treatment of a hydrogen chloride gas evolved during the reaction and the material quality for a vacuum generator required.

Therefore, in order to industrially synthesize β-chloropivaloyl chloride with a high selectivity, the reaction must be carried out at a high temperature.

Further, in the method described in Japanese Patent Publication No. 46046/1972, the reaction rate of a clorination on side chains is slow, and thus, this method is not considered to be effective on the whole as the process for preparing β-chloropivaloyl chloride.

SUMMARY OF THE INVENTION

Accordingly, an object of the present invention is to provide a method for synthesizing β-chloropivaloyl chloride by which the production of by-products such as dichloro-compounds is inhibited and a reaction is achieved with a high efficiency.

It is another object of the present invention to provide a method for synthesizing β-chloropivaloyl chloride from pivalic acid with high selectivity.

Other objects and advantages of the present invention will become apparent during the following discussion of the accompanying drawings.

DETAILED DESCRIPTION OF THE INVENTION

Figure 1:
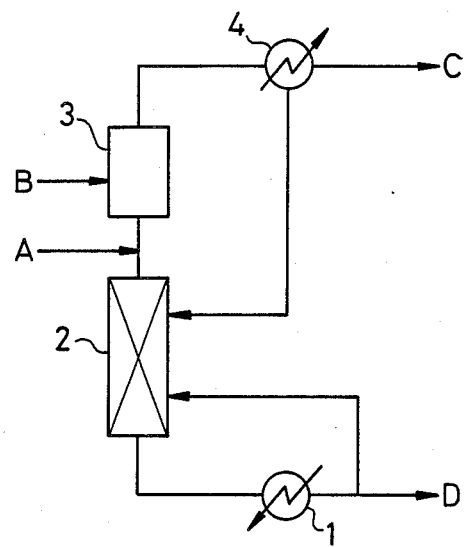
FIG. 1 is a flow sheet illustrating an embodiment of the present invention.

The present inventors have conducted a research with the intention of solving the above mentioned problems, and as a result, they have found that the temperature of a system can be lowered by employing the following process to inhibit the formation of by-products such as polymers and decomposition products, whereby the drawbacks of the conventional method described above can be overcome. The present invention, therefore, has been completed on the basis of this knowledge.

The process referred to above includes the following:

(1) First, chlorinating pivalic acid to form pivaloyl chloride.

(That is, in this step, pivaloyl chloride is formed from the raw material by the chlorination.)

(2) Second, chlorinating pivaloyl chloride in a gaseous phase, while it is distilled.

(That is, the reaction is caused to progress by bringing the vapor of pivaloyl chloride into contact with a chlorine gas. Therefore, filler is not used in a reaction portion, and the starting pivaloyl chloride material and the recovered pivaloyl chloride at a tower top need not be introduced into the reaction portion and may be introduced to a fractionating portion of a distillation tower).

According to the present invention there is provided a method for preparing β-chloropivaloyl chloride which is characterized by chlorinating pivalic acid to form pivaloyl chloride and reacting the resultant pivaloyl chloride with a chlorine gas in a gaseous phase.

In the present invention, pivaloyl chloride can be prepared, according to a known process per se, by reacting pivalic acid with thionyl chloride (Beilstein Band II H320) or with phosgene, or by reacting pivalic acid with trichromethylbenzenes in the presence of Lewis acid (Japanese Patent Application laid open No. 82336/1982). The pivaloyl chloride is commercially available.

The synthesis of β-chloropivaloyl chloride in the second step is carried out by the gaseous phase reaction. The boiling point of pivalic acid is from 163° to 164° C., whereas that of pivaloyl chloride is from 105° to 106° C. Accordingly, this step permits lowering the temperature of the reaction system remarkably.

With regard to a temperature for this reaction, a temperature at which pivaloyl chloride evaporates is sufficient, but in view of decomposition and the like, it is usually set to a level of 90° to 110° C.

A molar ratio of pivaloyl chloride to chlorine is usually within the range of 4:1 to 20:1, preferably 8:1 to 14:1. When the molar ratio deviates from the boundary of 4:1, i.e., when an amount of chlorine exceeds the upper limit, by-products such as dichloropivaloyl chloride and the like increase, which factor decreases selectivity disadvantageously. On the contrary, when the molar ratio deviates from the boundary of 20:1, i.e., when the amount of chlorine is too small, the yield will be low and the method itself will be impractical. Chlorine will take part in the reaction immediately after it is introduced. The reaction time is not limited in particular. It is preferred that the reaction is carried out under the irradiation of ultraviolet rays, but a small amount of irradiation suffices.

An example of the operation according to the present invention may be a continuous process or a batch process; one example of the continuous process is shown in FIG. 1. Referring now to a method in FIG. 1, reference numeral 1 represents a reboiler, 2 a distillation tower, 3 a gaseous phase reaction portion, and 4 a condenser. Symbol A denotes pivaloyl chloride which is being fed, and B denotes chlorine. Both the reactants are reacted with each other in the gaseous phase reaction portion 3, in which a side chain chlorination takes place to produce $\beta$-chloropivaloyl chloride. The reaction gas thus produced is then taken out through the upper portion of the gaseous phase reaction portion 3 and is afterward separated from hydrogen chloride C by the condenser 4. After this separation, the resultant condensate containing $\beta$-chloropivaloyl chloride is circulated toward the upper portion of the distillation tower 2, in which the desired $\beta$-chloropivaloyl chloride is further separated from unreacted pivaloyl chloride. The desired $\beta$-chloropivaloyl chloride is drawn out of the distillation tower 2 through the bottom thereof and is then taken out as $\beta$-chloropivaloyl chloride D via the reboiler 1. Unreacted pivaloyl chloride is returned to the gaseous phase reactive portion through the top portion of the distillation tower 2 and is then used as the starting material again. In the above operation, the condensate containing $\beta$-chloropivaloyl chloride from which hydrogen chloride has been separated may be circulated toward the lower portion of the gaseous phase reaction portion 3, instead of the circulation to the distillation tower 2 as described above.

In the above operation, the temperature in the gaseous phase portion 3 is within the range of 92° to 103° C., and at this time, the temperature on the bottom of the distillation tower is within the range of 165° to 175° C.

According to the method of the present invention, the production of $\beta$-chloropivaloyl chloride is achieved by first obtaining pivaloyl chloride and then carrying out its side chain chlorination employing a gaseous phase reaction. Thus, the method of the present invention has the following advantages:

(1) The formation of dichloro-compounds which are by-products can be reduced at a very low level, and reaction selectivity can be enhanced extremely.

(2) Since the present invention makes use of acid chloride instead of acid in the side chain chlorination, the following effects can be obtained:

(i) The reactions can be carried out at a much lower temperature, as compared with such a liquid phase method as in Japanese Patent Publication No. 46046/1972 as a consequence, the decomposition and the polymerization of the product can be inhibited (in the present invention the temperature on the tower bottom is as low as 105° to 175° C., but that in the conventional method is from 160° to 222° C.).

(ii) Further, much energy can be saved.

(iii) Since no specific heat transfer medium is required, the reaction apparatus for an industrial scale production can easily be designed.

(iv) The side chain chlorination is facilitated, and a smaller amount of unreacted chlorine remains.

DESCRIPTION OF THE PREFERRED EMBODIMENT

To further illustrate the present invention, and not by way of limitation, the following examples are given.

The conversion and the selectivity used in this specification can be defined as follows:

Conversion:
100-Content of unreacted pivaloyl chloride (%)
Selectivity:

$$\frac{\text{Content of } \beta\text{-chloropivaloylchloride (\%)}}{\text{Conversion (\%)}} \times 100$$

Figure 2:
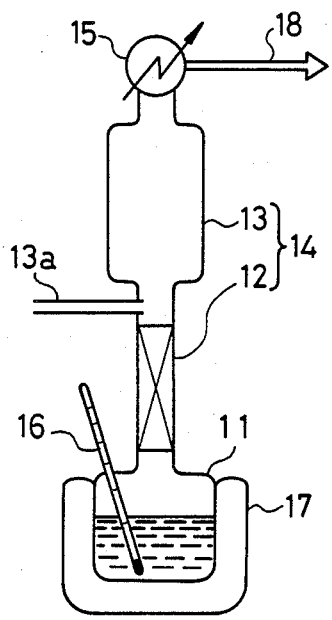
FIG. 2 is a schematic view of a reaction apparatus used in the practice of a method according to the present invention.

EXAMPLE $\beta$-Chloropivaloyl chloride was prepared by using a reaction apparatus shown in FIG. 2 in the following procedure: That is, as shown in FIG. 2, a distillation tower 14 was composed of a filled portion 12 and a gaseous phase reaction portion 13, and the filled portion 12 (which was filled with glass Raschig rings each having a diameter of 8 mm) was 40 mm in diameter and 600 mm in height and was disposed at the upper portion of a flask 11 which was equipped with a thermometer 16 and a heating portion 17. The gaseous phase reaction portion 13 was disposed on the filled portion 12, was made of a glass, and had a diameter of 35 mm and a height of 500 mm.

In the filled portion 12, a constant temperature was sufficiently kept up so as not to give rise to heat losses, and a cooler 15 was fixed on the top of the tower 14, by which a condensate was returned to the upper portion of the filled portion 12 and hydrogen chloride 18 was discharged from the reaction system. The reaction made progress as follows:

In the flask 11 were placed 241.2 g of pivaloyl chloride and the flask 11 was then heated by a heater 17. Chlorine was introduced into the gaseous phase reactive portion 13 so that a ratio of a pivaloyl chloride vapor:chlorine might be 12:1. At this time, the temperature of the tower bottom rose from 105° C. to 166° C.

After the reaction had been conducted for 10.5 hours, the tower bottom liquid was analyzed by gas chromatography, and the results obtained indicated that the tower bottom liquid was composed of 95.6 mol% of monochloropivaloyl chloride, 1.62 mol% of $\beta,\beta$-dichloropivaloyl chloride, 2.25% of $\beta,\beta'$-dichloropivaloyl chloride; a conversion of pivaloyl chloride which was the starting material was 99.7%; and the selectivity of monochloropivaloyl chloride was 95.8%.

The relation between the conversion and the selectivity of pivaloyl chloride in the gaseous chlorination which was obtained as discussed above is set forth in FIG. 3. In this drawing, curves (a), (b) and (c) represent the content of pivaloyl chloride, the content of $\beta$-chloropivaloyl chloride in the tower bottom liquid, and the selectivity of $\beta$-chloropivaloyl chloride, respectively.

Figure 3:
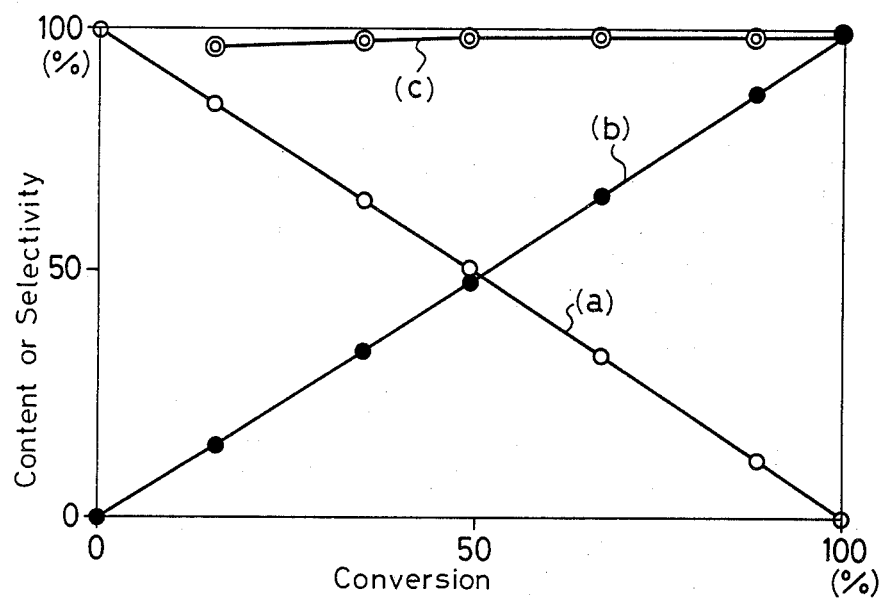
FIG. 3 is a graph showing the relation between conversion and selectivity in an example.

As is clear from FIG. 3, in the present invention, even when the conversion rises up to a level in the vicinity of 100%, by-products of dichloro-compounds such as $\beta,\beta$-dichloropivaloyl chloride and $\beta,\beta'$-dichloropivaloyl chloride are barely present, and the high selectivity of about 95% or more is always attained.

COMPARATIVE EXAMPLE

In a 200-ml glass four-necked flask equipped with a stirrer, a gas blowing pipe, a reflux condenser and a thermometer was placed 120.6 g of pivaloyl chloride, and chlorine was then blown into the liquid pivaloyl chloride at a feed rate of 4.8 l/hr.

While the reaction temperature was maintained at 90° C., a reaction was performed until a production ratio of monochloropivaloyl chloride reached to a maximum level.

The resultant reaction mixture was analyzed by the use of gas chromatography, and the results showed that the conversion of pivaloyl chloride was 86% and the selectivity of monochloropivaloyl chloride was 70%.

Figure 4:
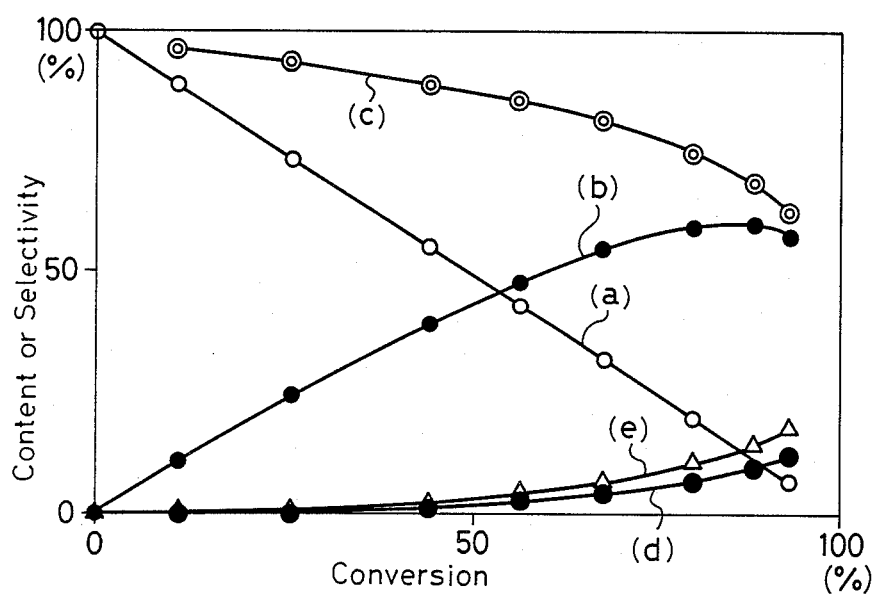
FIG. 4 is the graph showing a relation between the conversion and the selectivity in a comparative example.

Also, with regard to the chlorination of this pivaloyl chloride, the relation between the conversion and the selectivity was measured in the same manner as in the example. The results are shown in FIG. 4. In this drawing, curves (a), (b) and (c) represent the content of pivaloyl chloride, the content of β-chloropivaloyl chloride in the tower bottom liquid, and the selectivity of β-chloropivaloyl chloride, respectively. Further, curves (d) and (e) represent the content of β,β'-dichloropivaloyl chloride and the content of β,β-dichloropivaloyl chloride, respectively.

As is apparent from the results in FIG. 4, in the Comparative Example, by-products such as β,β-dichloropivaloyl chloride and β,β'-dichloropivaloyl chloride increase remarkably, as the conversion rises, with the result that the selectivity is lowered.

As many apparently widely different embodiments of this invention may be made without departing from the spirit and scope thereof, it is to be understood that the invention is not limited to the specific embodiment thereof except as defined in the appended claims.

What we claim is:

1. A method for preparing β-chloropivaloyl chloride comprising reacting pivaloyl chloride with a chlorine gas in a gaseous phase at a temperature of 90° to 110° C. wherein the molar ratio of pivaloyl chloride to chlorine is 4:1 to 20:1.

2. The method according to claim 1, wherein said gaseous phase reaction of pivaloyl chloride with said chlorine gas is carried out at a temperature of 92° to 103° C.

3. The method according to claim 1, wherein said molar ratio of pivaloyl chloride:chlorine is 8:1 to 14:1.

4. A method for preparing β-chloropivaloyl chloride comprising the steps of:

reacting pivaloyl chloride with a chlorine gas in a gaseous phase reaction area;

removing reaction gas thus formed to a condenser to separate hydrogen chloride from said reaction gas;

circulating a resultant condensate containing β-chloropivaloyl chloride to an upper portion of a distillation tower to separate β-chloropivaloyl chloride from unreacted pivaloyl chloride;

returning said unreacted pivaloyl chloride to said gaseous phase reaction area through said upper portion of said distillation tower; and recovering desired β-chloropivaloyl chloride from said distillation tower to separate β-chloropivaloyl chloride.

5. The method according to claim 4, wherein said chlorine gas is fed to said gaseous phase reaction area.

6. The method according to claim 4, wherein pivaloyl chloride is supplied into said gaseous phase reaction area from outside of the system.

7. The method according to claim 4, wherein said method is conducted continuously.

8. The method according to claim 1, wherein said molar ratio of pivaloyl chloride to chlorine is 12:1.

9. The method according to claim 4, wherein said gaseous phase reaction of pivaloyl chloride with said chlorine gas is carried out at a temperature of 90° to 110° C.

10. The method according to claim 9, wherein said gaseous phase reaction of pivaloyl chloride with said chlorine gas is carried out at a temperature of 92° to 103° C.

11. The method according to claim 4, wherein a molar ratio of pivaloyl chloride:chlorine is 4:1 to 20:1.

12. The method according to claim 11, wherein a molar ratio of pivaloyl chloride:chlorine is 4:1 to 20:1.

* * * * *